US006748276B1

(12) United States Patent
Daignault, Jr. et al.

(10) Patent No.: US 6,748,276 B1
(45) Date of Patent: Jun. 8, 2004

(54) NEUROMODULATION THERAPY SYSTEM

(75) Inventors: Richard J. Daignault, Jr., Frisco, TX (US); Gerhard Deffner, McKinney, TX (US); Rob Egemo, Plano, TX (US); John Erickson, Plano, TX (US); Robert W. Fee, Savannah, GA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 09/587,673

(22) Filed: Jun. 5, 2000

(51) Int. Cl.[7] .................................................. A61N 1/36
(52) U.S. Cl. .......................................... 607/46; 607/59
(58) Field of Search ............................ 607/46, 58, 117, 607/118, 2, 30, 59, 27; 600/27, 28; 128/920, 922

(56) References Cited

U.S. PATENT DOCUMENTS

| | | |
|---|---|---|
| 3,888,261 A | 6/1975 | Maurer |
| 4,459,989 A | 7/1984 | Borkan |
| 4,612,934 A | 9/1986 | Borkan |
| 4,793,353 A | 12/1988 | Borkan |
| 5,370,672 A | 12/1994 | Fowler et al. |
| 5,443,486 A | 8/1995 | Hrdlicka et al. ............... 607/59 |
| 5,938,690 A * | 8/1999 | Law et al. ..................... 607/46 |
| 6,208,902 B1 * | 3/2001 | Boveja ......................... 607/46 |
| 6,393,325 B1 * | 5/2002 | Mann et al. .................. 607/46 |

FOREIGN PATENT DOCUMENTS

EP  0 811 395 A2  12/1997

OTHER PUBLICATIONS

Richard B. North, et al., "Spinal cord stimulation for chronic, intractable pain: superiority of 'multi-channel' devices", *Pain*, 44 (1991), pp. 119–130.

Richard B. North, et al., "Automated 'pain drawing' analysis by computer-controlled, patient-interactive neurological stimulation system", *Pain*, 50 (1992), pp. 51–57.

Richard B. North, et al., "Patient-interactive, computer-controlled neurological stimulation system: clinical efficacy in spinal cord stimulator adjustment", *J. Neurosurg.*, 76 (Jun., 1992), pp. 967–972.

Richard B. North, "The Role of Spinal Cord Stimulation in Contemporary Pain Management", *APS Journal*, 2(2) (1993), pp. 91–99.

Richard B. North, et al., "Spinal Cord Stimulation for Chronic, Intractable Pain: Experience over Two Decades", *Neurosurgery*, vol. 32, No. 3, Mar. 1993, pp. 384–395.

Richard B. North, "Spinal Cord Stimulation for Chronic, Intractable Pain", *Electrical and Magnetic Stimulation of the Brain and Spinal Cord*, Raven Press, Ltd., New York, 1993, pp. 289–301.

Giancarlo Barolat, "Current Status of Epidural Spinal Cord Stimulation", *Neurosurgery Quarterly*, 5(2) (1995), pp. 98–124.

Advanced Neuromodulation Systems "COMPUSTIM™ SCS SYSTEM" Clinician Manual, Oct., 1997, pp. 1–48.

* cited by examiner

*Primary Examiner*—George R. Evanisko
(74) *Attorney, Agent, or Firm*—Koestner Bertani, LLP

(57) ABSTRACT

A neuromodulation therapy system includes a programmer and a stimulation system. The stimulation system is capable of storing multiple data sets, each data set effecting an independent therapy. The stimulation system includes a display mechanism that can display certain imagery to distinguish visually one therapy from another therapy.

24 Claims, 11 Drawing Sheets

| Program No. | Stim-set Quantity | Composite Graphic |
|---|---|---|

| Program No. | Stim-set No. | Freq. Value | Pulse Width Value | Electrode Config. | Phase | Min./Max. Amplitude | Stim-set Graphic |
|---|---|---|---|---|---|---|---|

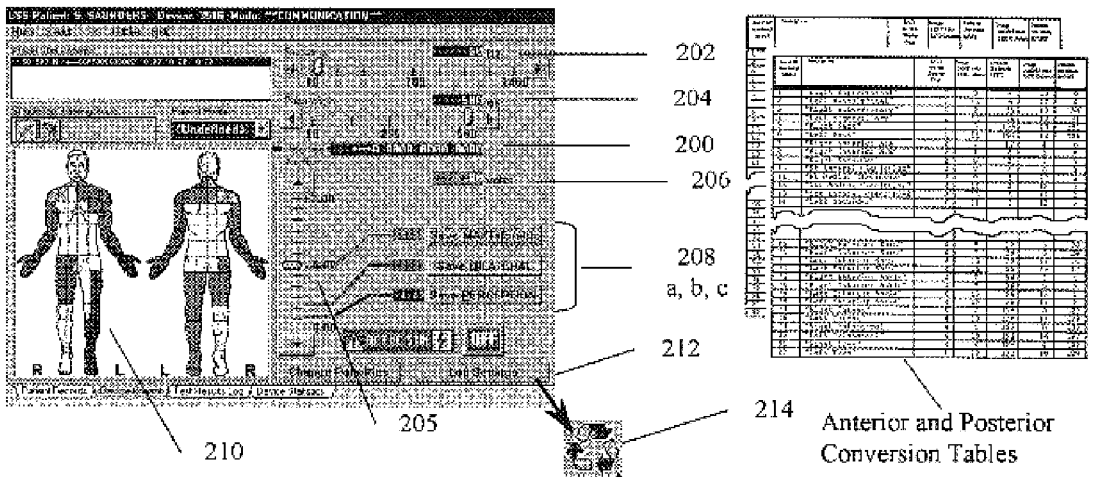
*FIG. 9A*
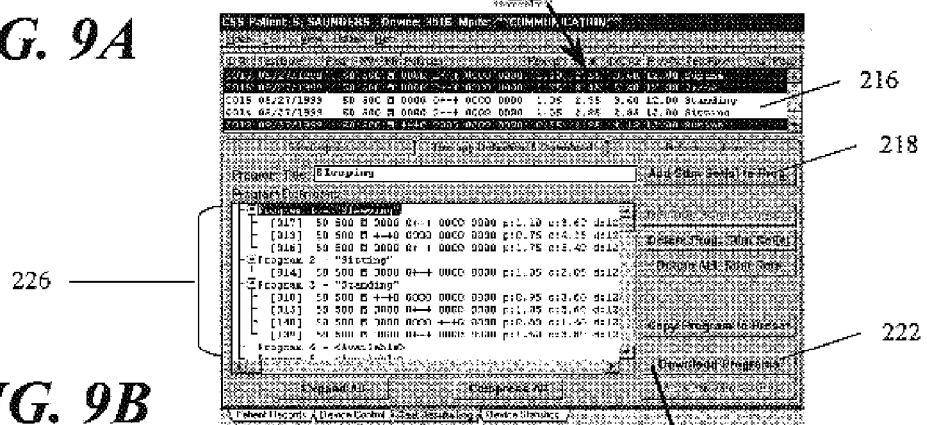
*FIG. 9B*
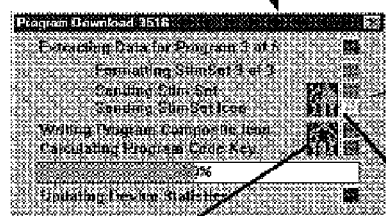
*FIG. 9C*
 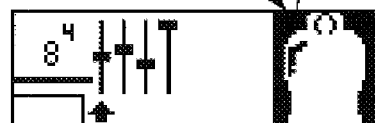
*FIG. 9D*  *FIG. 9E*

| Anterior Anatomy Area # | Description | LCD Screen Display Page | Image LEFT Side LCD Column | Column Bit Mask LEFT | Image RIGHT Side LCD Column | Column Bit Mask RIGHT |
|---|---|---|---|---|---|---|
| 1 | Right SupraOrbital | 1 | 9 | 4 | 10 | 6 |
| 2 | Left SupraOrbital | 1 | 11 | 6 | 12 | 4 |
| 3 | Right Submaxillary | 1 | 9 | 24 | 10 | 56 |
| 4 | Left Submaxillary | 1 | 11 | 56 | 12 | 24 |
| 5 | Right Neck | 1 | 9 | 128 | 10 | 192 |
| 6 | Left Neck | 1 | 11 | 192 | 12 | 128 |
| 7 | Right Exterior Arm | 2 | 3 | 12 | 4 | 6 |
| 8 | Right Interior Arm | 2 | 4 | 8 | 5 | 6 |
| 9 | Right Shoulder | 2 | 6 | 3 | 7 | 1 |
| 10 | Right Lateral Clavicular | 2 | 7 | 2 | 8 | 3 |
| 11 | Right Medial Clavicular | 2 | 9 | 3 | 10 | 3 |
| 12 | Left Medial Clavicular | 2 | 11 | 3 | 12 | 3 |
| 13 | Left Lateral Clavicular | 2 | 13 | 3 | 14 | 2 |
| 14 | Left Shoulder | 2 | 14 | 1 | 15 | 3 |
| 15 | Left Interior Arm | 2 | 16 | 6 | 17 | 8 |
| 16 | Left Exterior Arm | 2 | 17 | 6 | 18 | 12 |
| 17 | Right Exterior Elbow | 2 | 2 | 16 | 2 | 0 |
| 18 | Right Interior Elbow | 2 | 3 | 16 | 3 | 0 |
| 19 | Right Lateral Mammary | 2 | 7 | 12 | 8 | 12 |
| 20 | Right Medial Mammary | 2 | 9 | 12 | 10 | 12 |
| ... | | | | | | |
| 48 | Left Ulnar Palm | 3 | 20 | 6 | 20 | 0 |
| 49 | Left Median Palm | 3 | 19 | 6 | 19 | 0 |
| 50 | Left Thumb | 3 | 18 | 2 | 18 | 0 |
| 51 | Right Median Fingers | 3 | 2 | 8 | 2 | 0 |
| 52 | Right Ulnar Fingers | 3 | 1 | 8 | 1 | 0 |
| 53 | Left Ulnar Fingers | 3 | 20 | 8 | 20 | 0 |
| 54 | Left Median Fingers | 3 | 19 | 8 | 19 | 0 |
| 55 | Right Hip | 3 | 5 | 8 | 6 | 12 |
| 56 | Right Pubic | 3 | 7 | 12 | 8 | 12 |
| 57 | Right Perineum | 3 | 9 | 12 | 10 | 12 |
| 58 | Left Perineum | 3 | 11 | 12 | 12 | 12 |
| 59 | Left Pubic | 3 | 13 | 12 | 14 | 12 |
| 60 | Left Hip | 3 | 15 | 12 | 16 | 8 |
| 61 | Right Exterior Thigh | 3 | 5 | 240 | 6 | 240 |
| 62 | Right Interior Thigh | 3 | 7 | 240 | 8 | 240 |
| ... | | | | | | |
| 73 | Right Exterior Ankle | 4 | 7 | 96 | 7 | 0 |
| 74 | Right Interior Ankle | 4 | 8 | 96 | 8 | 0 |
| 75 | Left Interior Ankle | 4 | 13 | 96 | 13 | 0 |
| 76 | Left Exterior Ankle | 4 | 14 | 96 | 14 | 0 |
| 77 | Right Tarsal | 4 | 7 | 128 | 8 | 128 |
| 78 | Left Tarsal | 4 | 13 | 128 | 14 | 128 |
| 79 | Right Metatarsal | 4 | 5 | 192 | 6 | 192 |
| 80 | Left Metatarsal | 4 | 15 | 192 | 16 | 192 |
| 81 | Right Toes | 4 | 3 | 128 | 4 | 192 |
| 82 | Left Toes | 4 | 17 | 192 | 18 | 128 |

*FIG. 12*

| Posterior Anatomy Area # | Description | LCD Screen Display Page | Image LEFT Side LCD Column | Column Bit Mask LEFT | Image RIGHT Side LCD Column | Column Bit Mask RIGHT |
|---|---|---|---|---|---|---|
| 1 | Right Parietal | 1 | 9 | 4 | 10 | 6 |
| 2 | Left Parietal | 1 | 11 | 6 | 12 | 4 |
| 3 | Right Occipital | 1 | 9 | 24 | 10 | 56 |
| 4 | Left Occipital | 1 | 11 | 56 | 12 | 24 |
| 5 | Right Neck | 1 | 9 | 128 | 10 | 192 |
| 6 | Left Neck | 1 | 11 | 192 | 12 | 128 |
| 7 | Right Exterior Arm | 2 | 3 | 12 | 4 | 6 |
| 8 | Right Interior Arm | 2 | 4 | 8 | 5 | 6 |
| . | | | | | | |
| . | | | | | | |
| 21 | Left Interscapular | 2 | 11 | 12 | 12 | 12 |
| 22 | Left Scapular | 2 | 13 | 12 | 14 | 12 |
| 23 | Left Interior Elbow | 2 | 18 | 16 | 18 | 0 |
| 24 | Left Exterior Elbow | 2 | 19 | 16 | 19 | 0 |
| 25 | Right Infrascapular | 2 | 7 | 48 | 8 | 48 |
| 26 | Left Midback | 2 | 9 | 48 | 10 | 48 |
| 27 | Right Midback | 2 | 11 | 48 | 12 | 48 |
| 28 | Left Infrascapular | 2 | 13 | 48 | 14 | 48 |
| 29 | Right Exterior Forearm | 2 | 1 | 192 | 2 | 96 |
| 30 | Right Interior Forearm | 2 | 2 | 128 | 3 | 96 |
| 31 | Right Lateral Lumbar | 2 | 7 | 192 | 8 | 192 |
| 32 | Right Medial Lumbar | 2 | 9 | 192 | 10 | 192 |
| 33 | Left Medial Lumbar | 2 | 11 | 192 | 12 | 192 |
| 34 | Left Lateral Lumbar | 2 | 13 | 192 | 14 | 192 |
| 35 | Left Interior Forearm | 2 | 18 | 96 | 19 | 128 |
| 36 | Left Exterior Forearm | 2 | 19 | 96 | 20 | 192 |
| 37 | Right Exterior Wrist | 3 | 1 | 1 | 1 | 0 |
| 38 | Right Interior Wrist | 3 | 2 | 1 | 2 | 0 |
| 39 | Left Interior Wrist | 3 | 19 | 1 | 19 | 0 |
| 40 | Left Exterior Wrist | 3 | 20 | 1 | 20 | 0 |
| 41 | Right Thumb | 3 | 3 | 2 | 3 | 0 |
| 42 | Right Median Palm | 3 | 2 | 6 | 2 | 0 |
| 43 | Right Ulnar Palm | 3 | 1 | 6 | 1 | 0 |
| 44 | Right Coxal | 3 | 7 | 3 | 8 | 3 |
| 45 | Right Low Back | 3 | 9 | 3 | 10 | 3 |
| 46 | Left Low Back | 3 | 11 | 3 | 12 | 3 |
| 47 | Left Coxal | 3 | 13 | 3 | 14 | 3 |
| . | | | | | | |
| . | | | | | | |
| 63 | Left Interior Thigh | 3 | 13 | 240 | 14 | 240 |
| 64 | Left Exterior Thigh | 3 | 15 | 240 | 16 | 240 |
| 65 | Right Exterior Knee | 4 | 5 | 3 | 6 | 3 |
| 66 | Right Interior Knee | 4 | 7 | 3 | 8 | 3 |
| 67 | Left Interior Knee | 4 | 13 | 3 | 14 | 3 |
| 68 | Left Exterior Knee | 4 | 15 | 3 | 16 | 3 |
| 69 | Right Exterior Calf | 4 | 5 | 12 | 6 | 28 |
| 70 | Right Interior Calf | 4 | 7 | 28 | 8 | 28 |
| 71 | Left Interior Calf | 4 | 13 | 28 | 14 | 28 |
| 72 | Left Exterior Calf | 4 | 15 | 28 | 16 | 12 |
| . | | | | | | |
| . | | | | | | |
| 82 | Left Toes | 4 | 17 | 192 | 18 | 128 |

*FIG. 13*

NEUROMODULATION THERAPY SYSTEM

FIELD OF THE INVENTION

The present invention relates to a system that is capable of storing multiple data sets, which are not otherwise identifiable but for individual execution of such data sets; however, the system includes a display mechanism to display certain visual imagery to enable the functionality of each data sets to be distinguished.

BACKGROUND OF THE INVENTION

Application of specific electrical fields to spinal nerve roots, the spinal cord, and/or other nerve bundles for the purpose of chronic pain management has been actively practiced since the 1960s. While a precise understanding of the interaction between the applied electrical energy and the nervous tissue is not fully appreciated, it is known that application of an electrical field to spinal nervous tissue (i.e., spinal nerve roots and spinal cord bundles) can effectively interfere with the transmission of certain pain signals through such nervous tissue. More specifically, applying particularized electrical pulses to spinal nervous tissue that corresponds to regions of the body afflicted with chronic pain can induce paresthesia, or a subjective sensation of numbness or tingling, in the pain-afflicted regions. Depending on the individual patient, paresthesia can effectively "mask" certain pain sensations to the brain.

The above description uses the term "particularized" to denote that the applied electrical energy is intended to be focused on the specific spinal nervous tissue associated with the afflicted bodily regions. Care should be taken to avoid over stimulating the targeted nervous tissue, as over stimulation could lead to paresthesia being perceived in non-afflicted regions or, alternatively, feelings of discomfort.

As a first step to delivering effective electrical energy to targeted nervous tissue, the source of the electrical energy must be positioned proximate to such nervous tissue. Electrical energy is commonly delivered through conductive electrodes positioned external to a patient's dura layer, a structure that surrounds the spinal cord. Electrodes are carried by two primary vehicles: the percutaneous catheter and the laminotomy lead. Percutaneous catheters and laminotomy leads will be collectively referred to as "stimulation leads."

Percutaneous catheters, or percutaneous leads, commonly have two or more electrodes (for example, two, four, and eight) and are positioned above the dura layer through the use of a Touhy-like needle that passes through the skin, between desired vertebrae, and opens above the dura layer. Laminotomy leads have a thin paddle configuration and typically possess a plurality of electrodes (for example, two, four, eight, or sixteen) arranged in one or more columns. Surgical intervention is required for implanting laminotomy leads. In particular, a partial laminectomy is required, which involves the resection and removal of certain vertebral tissue to allow both access to the dura and proper positioning of the laminotomy lead.

Assuming that physical placement of the electrical energy source can be achieved, specific "selection" of the targeted nervous tissue from an encompassing tissue bundle is achieved through refinement of the delivered electrical energy. To this end, the delivered electrical energy is defined by an electrode configuration and an electric pulse waveform, or collectively a "stimulation setting."

The overall form of the delivered electrical energy is defined by the polarity of each electrode of the stimulation lead. With modern stimulation systems, each electrode can assume a positive polarity (an anode), a negative polarity (a cathode), or an off-state. The collective definition of the polarities of each electrode of a stimulation lead is described as an "electrode configuration."

The electric pulse waveform defines the nature of the signal delivered through the active electrodes. Of course, an electric pulse waveform is defined by a plurality of variables, including: pulse width ($\mu$s) (i.e., the duration in which the pulse is in a high state), frequency (Hz), amplitude (V), and sometimes phase (i.e., mono-phasic or bi-phasic). For purposes of description, a collection of these variables to define a single waveform will be referred to as a "treatment parameter set."

Identifying an optimum stimulation setting—one that masks a maximum quantity of pain with minimum over stimulation—can be time consuming and difficult. In particular, not even considering the endless combinations that can be effected by modifying the variables of a treatment parameter set, an eight-electrode stimulation lead offers 6,050 possible electrode combinations.

As may be understood from the above description, a single stimulation setting corresponds to a single treatment parameter set and a single electrode configuration. Consequently, each stimulation setting typically addresses only a single localized region of the body. If a patient experiences complex pain (i.e., pain that extends across multiple or varied regions of the body), then multiple stimulation settings may be required to address such pain. Further yet, different stimulation settings may be required for different times of the day or for different activities within the day, whereas changes in body position (e.g., lying down, sitting, standing) may impair or alter the effectiveness of any one stimulation setting.

FIG. 1 illustrates a modern, radio frequency (RF) stimulation system 1000. In particular, the system 1000 includes an external transmitter 1002 that is connected to an antenna 1004. Internally, a receiver 1008 is connected to at least one stimulation lead 1010 (and 1012), which in this instance is illustrated having eight electrodes 1010*a–h* (and 1012*a–h* for stimulation lead 1012). The receiver 1008 communicates, via an antenna 1006, with the transmitter 1002 through the skin 1032 of a patient.

Stimulation settings are stored within a memory of the transmitter 1002. Stimulation settings can be programmed into the transmitter 1002 using transmitter-based controls (not shown) or using a computer 1028 (e.g., U.S. Pat. No. 5,938,690 to Law et al.) through a removable connection 1030. Operatively, stimulation settings are imposed on a RF carrier signal and passed to the receiver 1008 through the skin 1032 to effect stimulation through electrodes 1010*a–h* and 1012*a–h*.

The system 1000 allows the storage and application of 1–24 stimulation settings. Each stimulation setting is numerically represented (i.e., "1", "2", "3", etc.) based on an order of input into the transmitter 1002. The transmitter 1002 executes all stored stimulation settings sequentially, based on the settings' respective numerical representations. The execution of "adjacent" stimulation settings is made within a fixed time interval, such interval being of such a duration that switching between adjacent stimulation settings is largely imperceivable to the patient.

To this end, the conventional system would enable up to 24 different pain areas to be addressed. However, short of re-programming the stored stimulation settings, this system does not readily allow changes in stimulation settings for changes in activities or patient posture. Moreover, with each stimulation setting being simply represented by an alphanumeric representation, a patient or practitioner must maintain a separate log that correlates each stimulation setting with its stimulation effect. Otherwise, the patient would be required to execute each stored stimulation setting to appreciate its consequence.

Accordingly, a need exists for a stimulation system that provides a user substantive information regarding the effects or intended application of a stored stimulation setting.

A further need exists for a stimulation system that allows stored stimulation settings to be both readily and arbitrarily grouped, whereas each stimulation setting of a group is directed to addressing a common condition, and multiple groups are available for execution.

SUMMARY OF THE INVENTION

An object of the present invention is to overcome the known limitations of current neuromodulation systems described above.

Another object of the present invention is to provide a display mechanism for a user-portion of a neuromodulation system that conveys graphical information to a user regarding the intended effect of a stimulation setting.

To this end, one aspect of the present invention is directed to a tissue stimulation system having a transmitter, a receiver for implantation within a patient, and at least one multi-electrode, implantable stimulation lead. The stimulation lead is electrically connectable to the receiver. The transmitter is adapted to transmit stimulation data to the receiver, which effects delivery of electrical energy through the connected stimulation lead. Importantly, the delivered electrical energy is defined by stimulation setting(s).

Unlike known systems, the system of this aspect includes a memory adapted to store at least two programs, each program including a plurality of stimulation settings, a selector, and a controller. The selector operatively effects a selection of a stored program. The controller executes any selected programs, such involving the conversion of a stimulation setting of the selected program to stimulation data for transmission to the receiver.

For a neuromodulation system having a memory to store a plurality of independent instructions to effect an equal number of stimulation profiles, another aspect of the present invention is directed to a method for providing an identifier to enable a visual recognition of a functionality of each instruction. The steps for such provision include creating an instruction data file, which includes a plurality of variables that operatively defines a therapeutic application, to effect a stimulation profile when executed; and generating a graphical anatomical representation that effectively depicts a perceived stimulation profile. From this action, the anatomical representation is assessed so to generate a representative graphical image. With such image, the instruction data file is modified to include data corresponding to such representative graphical image.

Other objects and advantages of the present invention will be apparent to those of ordinary skill in the art having reference to the following Specification together with the drawings.

BRIEF DESCRIPTION OF THE DRAWINGS

Referring now to the drawings in which like reference numerals and letters indicate corresponding elements throughout the several view, if applicable:

FIGS. 9A through 9E illustrate various screen shots from software (subject to execution by a computer of the system of FIG. 2) and related transmitter displays, that operatively relate to the identification, setting, selection, and downloading of one or stimulation programs;

FIG. 12 partially illustrates a conversion table that includes data that establishes a graphical relationship among the display of the transmitter of FIG. 3, the composite bodily graphic of FIG. 11, and the anterior view of the bodily image graphic of FIG. 10;

FIG. 13 partially illustrates a conversion table that includes data that establishes a graphical relationship among the display of the transmitter of FIG. 3, the composite bodily graphic of FIG. 11, and the posterior view of the bodily image graphic of FIG. 10;

DETAILED DESCRIPTION OF THE PREFERRED EMBODIMENTS

Various embodiments, including preferred embodiments, will now be described in detail below with reference to the drawings.

Figure 1:
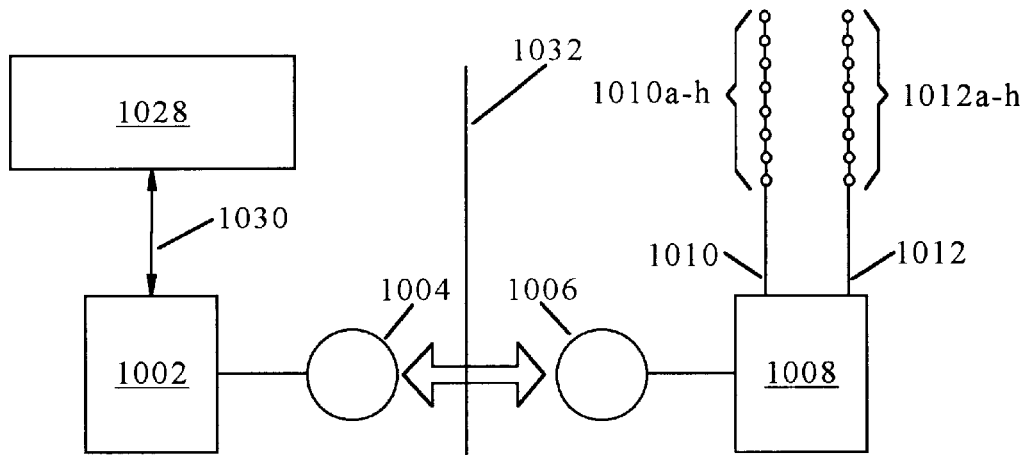
FIG. 1 is a schematic representation of a conventional radio-frequency neuromodulation system.
Figure 2:
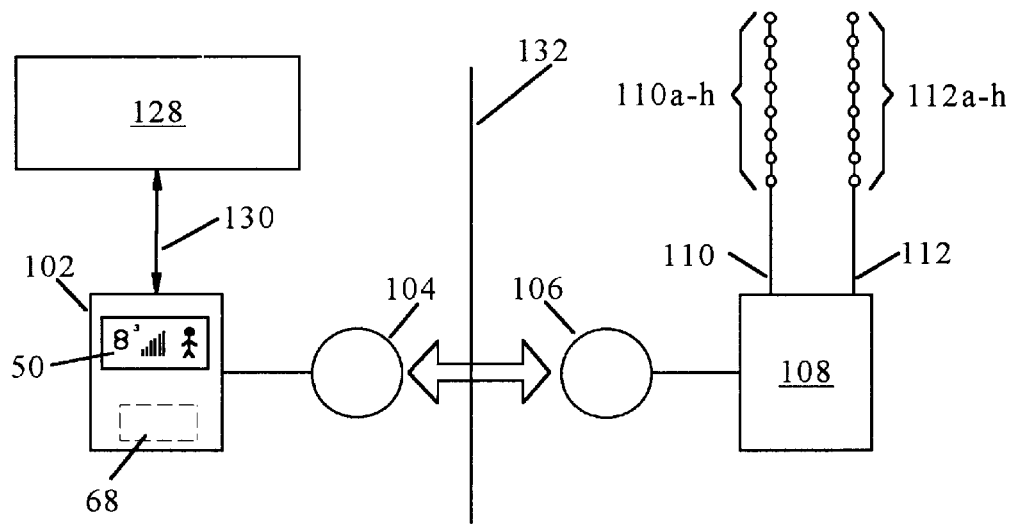
FIG. 2 is a schematic representation of a radio-frequency neuromodulation system in accordance with the present invention.

FIG. 2 illustrates one embodiment of a system in accordance with the present invention. The system 100 includes an external transmitter 102 that is connected to an antenna 104. Internally, a receiver 108 is connected to at least one stimulation lead 110 (and 112), which in this instance is illustrated having eight electrodes 110*a–h* (and 112*a–h* for stimulation lead 112). The receiver 108 communicates, via an antenna 106, with the transmitter 102 through the skin 120 of a patient. While the receiver 108 can include an internalized power source, it is more likely that the receiver 108 is powered by the carrier wave transmitted by the transmitter 102.

The computer 116 is a general-purpose computer that includes executable software. The computer 116 is capable of receiving input via its display (i.e., touch screen) or through a mouse or a stylus (not shown). While not critical to the invention, the computer 128 preferably operates in a Windows™-based environment. The computer 128 should include, or otherwise be connectable to, a display (or other output device) having a sufficient resolution so as to clearly present the visual information required by the present invention, such information being discussed in greater detail below.

The computer 128 is connectable to the transmitter 102 through a cable 130. In particular, it is preferable that the cables 130 extend between a standard RS232 serial port of the computer 128 and a serial connector (not shown) on the transmitter 102. Alternatively, the computer 128 and the transmitter 102 could be "connected" using an infrared transmission, a radio-frequency transmission, or an ultrasonic transmission.

The communication protocol used between the computer 128 and the transmitter 102 is preferably conventional, using traditional message blocks. Such message blocks incorporating message identification, type, data, checksum, and length fields. Component responses to data transmissions are likewise traditional, i.e., using ACK and NACK signals.

Figures 3, 4:
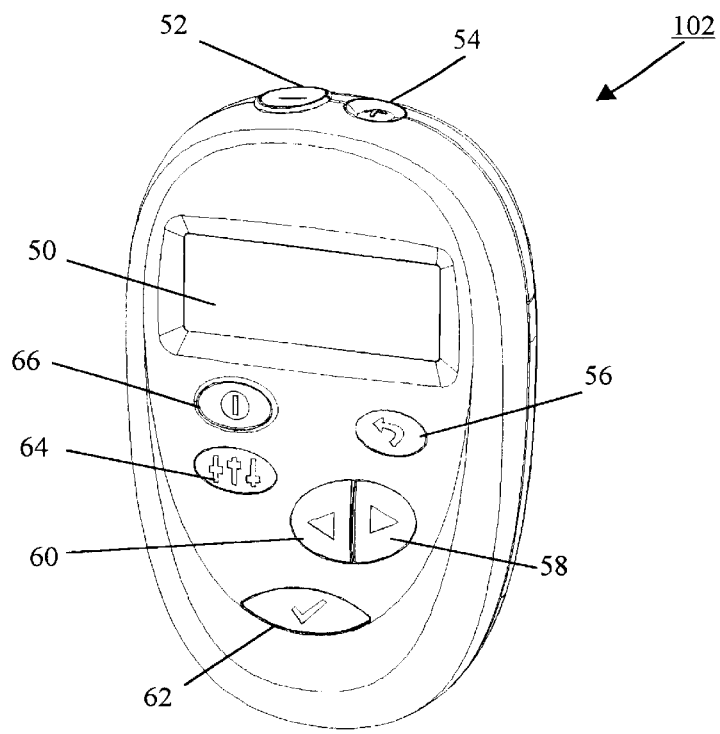
FIG. 3 illustrates a radio-frequency transmitter for use in the system of FIG. 2.
FIG. 4 schematically illustrates both a program data file and a stimulation setting data file operatively stored within the transmitter of FIG. 3.

FIG. 3 illustrates one embodiment of the transmitter 102. The transmitter includes a display 50. In a preferred embodiment, the display 50 has a resolution that allows alphanumeric and limited graphics data to be displayed, whether in monochrome or in color. In a preferred embodiment, the display 50 is a 100 column×32 row, monochrome LCD. While the specific controls are not necessarily critical to the invention, such will be at least mentioned here for reference.

User controls 52 and 54 function to respectively decrease and increase certain definable variables, e.g., stimulation amplitude. User control 56 functions to "cancel" an input or screen selection. User controls 58 and 60 are scroll controls, to enable a user to scroll through various presented options. User control 62 is an "enter" key, wherein inputs or options are selectable through actuation of user control 62. User control 64 is a "balance" key, which enables individual amplitude adjustment for each available stimulation setting of a program, its use will be discussed further below. Finally, user control 66 is a power switch.

The transmitter 102 functions to receive and store one or more stimulation settings. Stimulation settings can be entered or modified through the user controls 52, 54, and 58–64 and/or through the connected computer 128. Stimulation settings are stored in a non-volatile memory 68. Memory 68 requires a capacity sufficient to store a prescribed number of programs, and each program can include multiple stimulation settings. In a preferred embodiment, the transmitter 102 can operatively maintain at least two programs, each program including at least two stimulation settings. In a more preferred embodiment, the transmitter 102 can operatively maintain more than ten programs, each program maintaining no more than ten stimulation settings. In a most preferred embodiment, the transmitter 102 can operatively maintain twenty-four programs, and each program can maintains eight stimulation settings.

FIG. 4 illustrates a program data file as maintained in the transmitter 102, and more particularly, within the memory 68. The program data file includes space for a program number, a quantity of stimulation settings within the program, composite graphic data, and a maximum number of stimulation setting files. Each stimulation setting data file includes space for a program number, a stimulation setting number, a frequency value, a pulse width value, an electrode configuration (to define the state for each of the connected electrodes 110a–h and 112a–h), minimum and maximum amplitude limitations, and graphics data.

Operatively, for an active program, a microprocessor (not shown) within the transmitter 102 reads the memory 68 and extracts the program-specific data. The program-specific data is displayed in the display 50. An example of such a display is shown in FIG 5.

Figure 5:
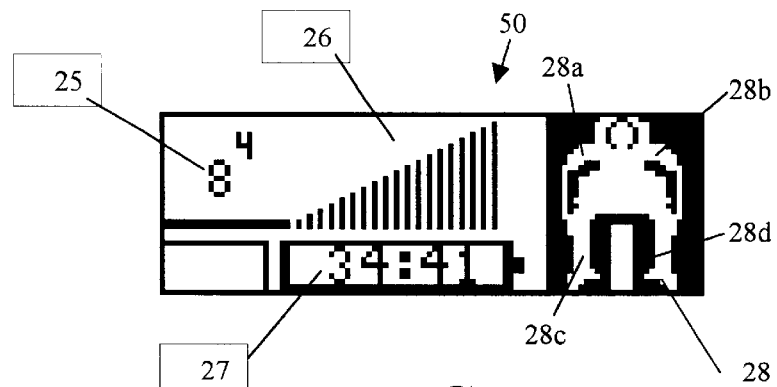
FIG. 5 illustrates one possible display arrangement presentable on a display of the transmitter of FIG. 3.

In reference to FIG. 5, region 25 indicates that program no. 8 is active, and that this program includes four stimulation settings. Region 26 depicts an overall-amplitude control adapted to control commonly an amplitude value for all stimulation settings of the active program. The overall-amplitude control is managed using user controls 52 and 54. In region 27, a battery life indicator is provided. While the battery life indicator is shown reflecting a specific time format (i.e., hours:minutes), such indicator could also display a relative time remaining using a variably filled battery form. Lastly, region 28 includes a composite graphic, which is formed from graphics data contributed from each of the stimulation settings of the program. The "composite" bodily graphic readily conveys to a user which regions of the patient's body are addressed by the current program. In particular reference to the illustrated graphic of region 28, program no. 8 effects stimulation in the right arm 28a, the left arm 28b, the right leg 28c, and the left leg 28d.

Figure 6:
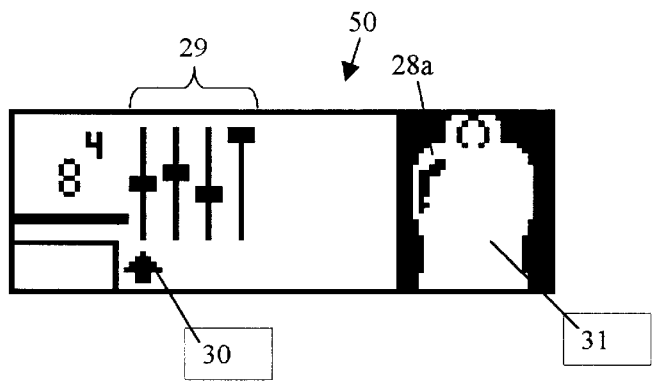
FIG. 6 illustrates another possible display arrangement presentable on the display of the transmitter of FIG. 3.

Of note, while FIG. 5 illustrates an overall-amplitude control, the transmitter 102 also allows the amplitude of each stimulation setting to be individually modified. Accordingly, delivered energy is governed by (i) individual amplitude settings, which are confined between minimum and maximum amplitude limits as defined in the respective stimulation setting data files and (ii) the overall-amplitude control. In regard to the latter, if the overall-amplitude control is set, for example, at 30% of maximum, each stimulation setting will realize only 30% of its set amplitude. FIG. 6 illustrates an example display that enables the individual adjustment of each of the stimulation settings of the program illustrated in FIG 5.

In reference to FIG. 6, arrow 30 indicates which stimulation setting amplitude is subject to modification. Control of arrow 30 is performed by user controls 58 and 60. Selection of a stimulation setting is effected by actuation of user control 62. Region 29 reflects respective "slider" controls for each stimulation setting. The individual minimum value (i.e., lower position of each slider) and maximum value (i.e., upper position of each slider) is dictated by the provided minimum and maximum amplitude limits, which (has stated above) are set within the individual stimulation setting files. Gradation fineness along each slider is a function of the differential between the maximum and minimum amplitude limits.

The display of region 31 is a function of the position of the arrow 30. In particular, the displayed graphic reflects the bodily region addressed by the selected stimulation setting. In this instance, the right arm 28a is shown (of note, this right arm representation is also a part of the composite graphic displayed in FIG. 5).

For this particular embodiment, the display of FIG. 6 is accessed by actuation of user control 64.

For safety purposes, it is preferred that modification of individual amplitude settings cannot occur unless the overall-amplitude is set to a low percentage value, e.g., 0%.

Focusing on the actual delivery of stimulation, for each stimulation setting, the microprocessor reads such stimulation setting from the active program, effects a multiplexing of the substantive data, or treatment parameter set (i.e., frequency, pulse width, phase, and electrode configuration) and a separately-stored, related amplitude value, and drives the delivery of the multiplexed data to a modulator (not shown) for preparation and combination with a generated RF carrier wave. The data-supporting carrying carrier wave is then passed to the antenna 104, which forwards the integrated stimulation setting (i.e., electrode configuration and waveform definitional variables) and carrier wave, which represents' a source of power for the receiver 108, to the antenna 106 and the connected receiver 108.

Figure 16A:
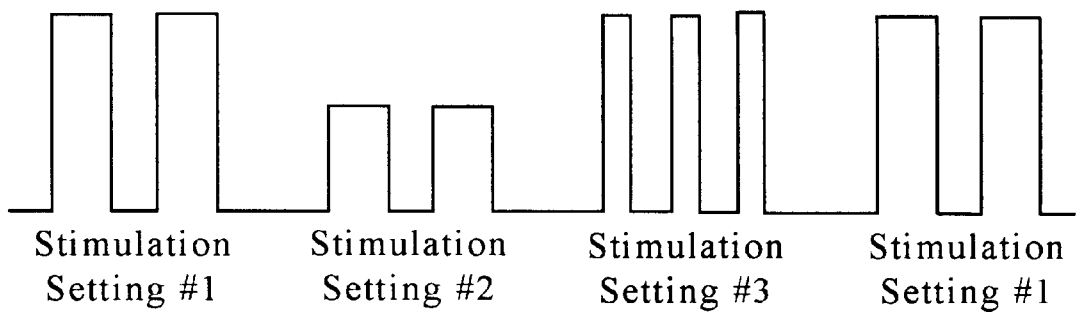
FIGS. 16A and 16B illustrate alternative methods of delivering multiple stimulation settings.
Figure 16B:
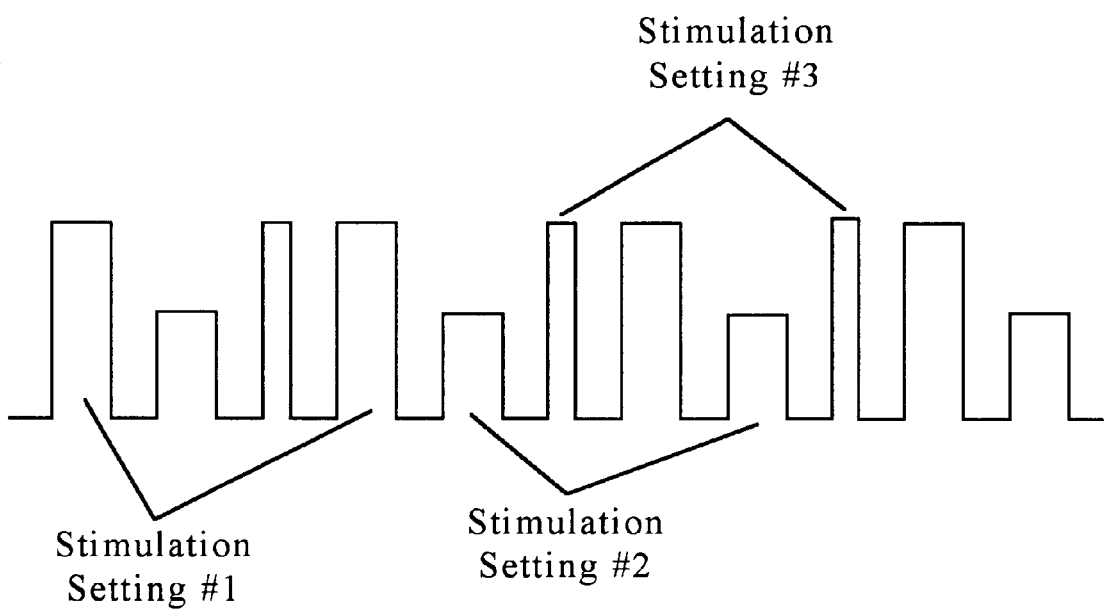

For a program having multiple stimulation settings, the microprocessor automatically cycles through each of the stimulation settings, executing each setting in a manner consistent with the above description. The microprocessor controls the time that any one stimulation setting is executed. For example, the microprocessor could define a specific period (e.g., 10 milliseconds), a period based on a frequency of the stimulation setting (e.g., two cycles, three cycles), or a combination of both (e.g., at least two cycles but not less than 10 milliseconds). Consistent with known systems, it is preferable that any time between executed stimulation settings be negligible so that a patient cannot readily perceive a transition between adjacent stimulation settings. As a further alternative, the microprocessor could execute one stimulation setting per pulse, thus creating a truly "seamless" therapy application. These alternatives are illustrated in FIGS. 16A AND 16B.

Multiple programs, which include one or more stimulation settings, can be used to address the shortcomings of the current art described earlier. Specifically, the user can establish different programs to address different activities as well as different postures. When the transmitter 102 has received multiple programs, the user actuates a user control of the transmitter 102 (e.g., the user controls 58 or 60) to access a program selection mode (indicated by a "P" in the lower left-hand corner of the display 50). Upon actuation of the user control 62, controls 58 and 60 are then used to scroll through the possible stored programs (FIGS. 7A–7D). Selection of any one program is effected through actuation of the user control 62. Of note, the illustrated graphics of the regions 28 of FIGS. 7A–7D reflect the different stimulation option available: left and right legs (PROGRAM 2); upper torso (PROGRAM 3); left and right arms and lower back (PROGRAM 4); and left and right arms and left and right legs (PROGRAM 5).

While the above discussion has focused on the user-portion of the present invention, the following discussion will be particularly directed to the software that is executed by the computer 128. In a general sense, the software offers the following features:

patient entry and identification;

real-time definition and testing of stimulation parameters;

documentation of tested stimulation results via graphical stimulation map(s);

storage of tested parameters, including graphical stimulation map(s);

review and selection of tests results for therapy definition;

conversion of graphical stimulation map(s) for use by the user device (e.g., transmitter 102); and download of defined therapies to the user device.

Figure 8:
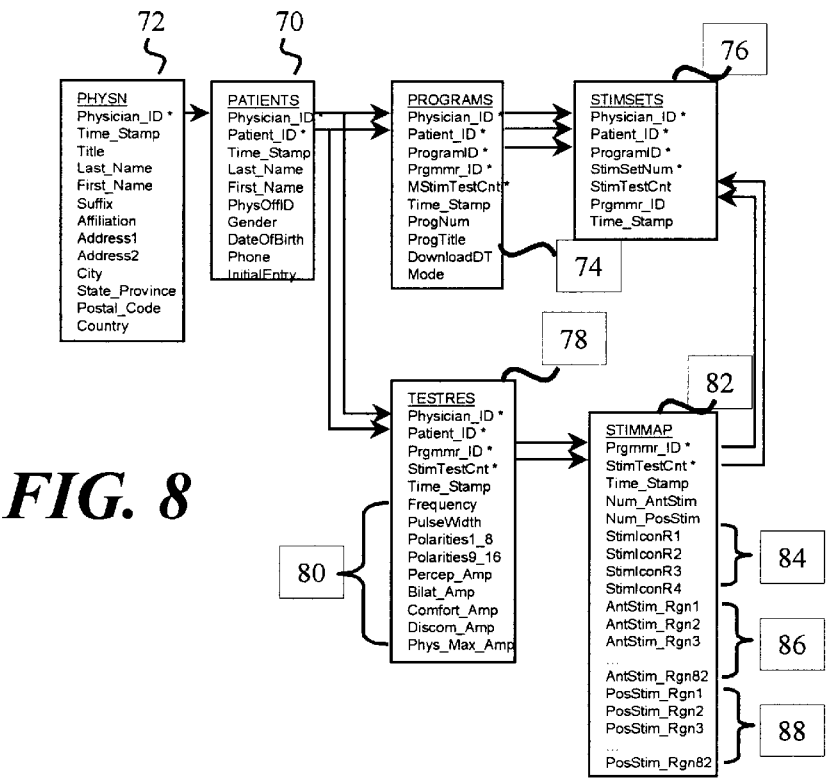
FIG. 8 schematically illustrates a database structure employed by software subject to execution by a computer of the system of FIG. 2.
Figures 7A, 7B, 7C, 7D:
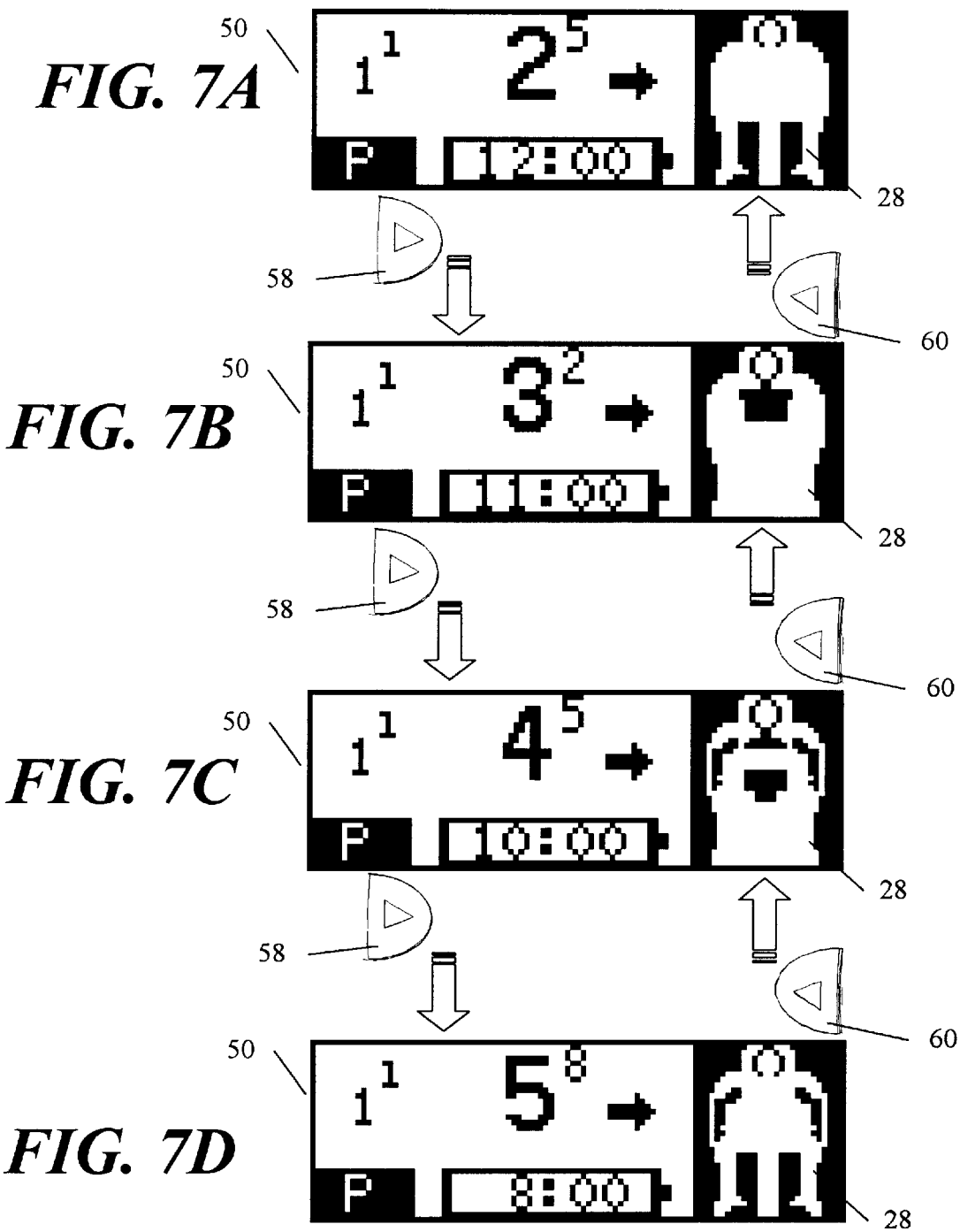
FIGS. 7A through 7D illustrate various display arrangements presentable on the display of the transmitter of FIG. 3 in a program selection mode.

Of the features above, "patient entry and identification" concerns the interface and record-keeping processes to manage the records stored within the computer 128. Reference is hereby made to FIG. 8, which illustrates the database structure used by the software. As can be seen in this figure, each record is indexed by a patient identification (e.g., a patient name), and in many instances, the patient's physician for verification. The PATIENTS and PHYSN tables 70 and 72 cooperate to maintain various, common identification and personal information, including: a patient name, physician, address, date of birth, etc. The means used to obtain this information, and even the information itself, is not essential to the present invention, excepting its role as a basis to establish an effective relational database.

In continued reference to FIG. 8, the lines and arrows connecting the various tables illustrate a preferred structure that establishes relationships and avoids duplication of data. Relationships between database tables are designated by a "*". Moreover, as a further example of this reduction in storage overhead, the TESTRES table 80 is used for both storage of tests and program definition. When considering the relational dependency of the STIMMAP table 82, there is need for only one stimulation image for every test (i.e., stimulation setting). While the present system could provide for multiple images (or the data representative of multiple images) to be recorded for each stimulation setting, at least this embodiment does not incorporate such variation. Thus, there is a one-to-one correspondence between each test result entry and the STIMMAP table 82.

Real-time Definition and Testing of Stimulation Parameters

In explaining the process of real-time definition and testing of stimulation parameters, reference will be made to the screen shot of the software reproduced in FIG. 9A. The illustrated screen is the "stimulation parameter adjustment and testing screen." To define a stimulation parameter, the following steps are followed:

Step #1: With an amplitude set to 0 V (Field 206), a practitioner defines an electrode configuration (Field 200), a frequency value (Field 202), and a pulse width value (Field 204).

Step #2: The amplitude "slider" (Field 205) is adjusted, and a patient response is recorded at the amplitude where stimulation is first perceived using screen button 208a.

Figure 10:
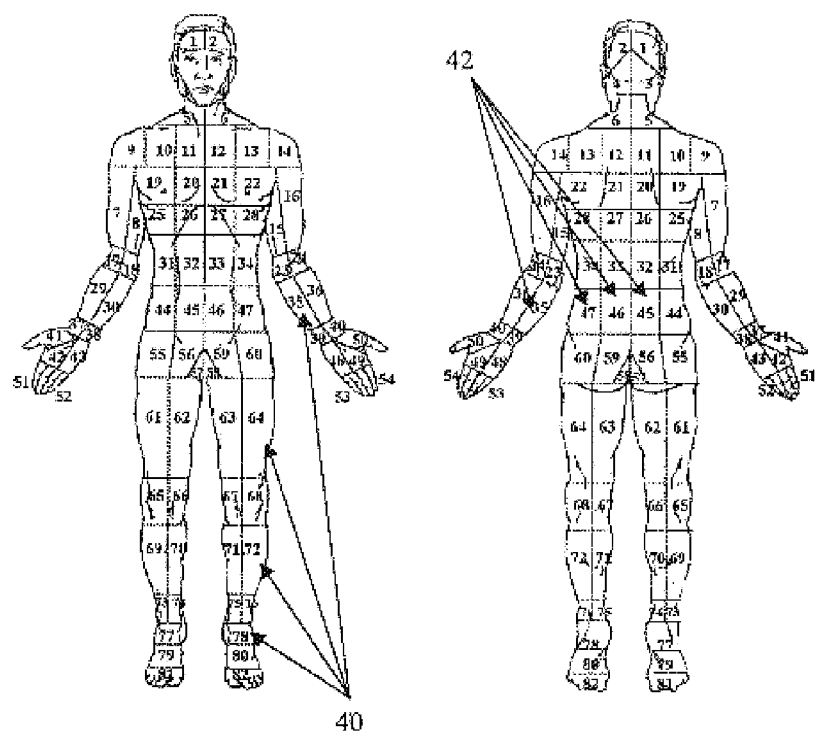
FIG. 10 illustrates anterior and posterior views of a bodily image graphic displayed by software subject to execution by a computer of the system of FIG. 2.

Step #3: The practitioner highlights all regions of the stimulation image (Region 210) that correspond to the actual perceived stimulation experienced by the patient. Of note, the stimulation diagram initially begins as only a bodily outline having a plurality of demarcated, non-highlighted regions (FIG. 10).

Step #4: The amplitude slider (Field 205) is again adjusted, and a patient response is recorded at the amplitude where bilateral stimulation is first perceived using screen button 208b.

Step #5: The practitioner highlights all regions of the stimulation image (Region 210) that correspond to the perceived feeling of the patient at such bilateral perception. Highlighting regions previously highlighted in Step #3 will result in such regions being updated with a bilateral-related value.

Step #6: The amplitude slider (Field 205) is again adjusted, and a patient response is recorded at the amplitude where maximum stimulation is first perceived using screen button 208c. Maximum stimulation is usually determined by the invocation of involuntary muscle reaction or other conditions that are equally undesirable.

Step #7: The practitioner highlights all regions of the stimulation image (Region 210) that correspond to the perceived feeling of the patient at motor perception. Highlighting regions previously highlighted in Steps #3 or Steps #5 will result in such regions being updated with a motor-related value.

Figure 14:
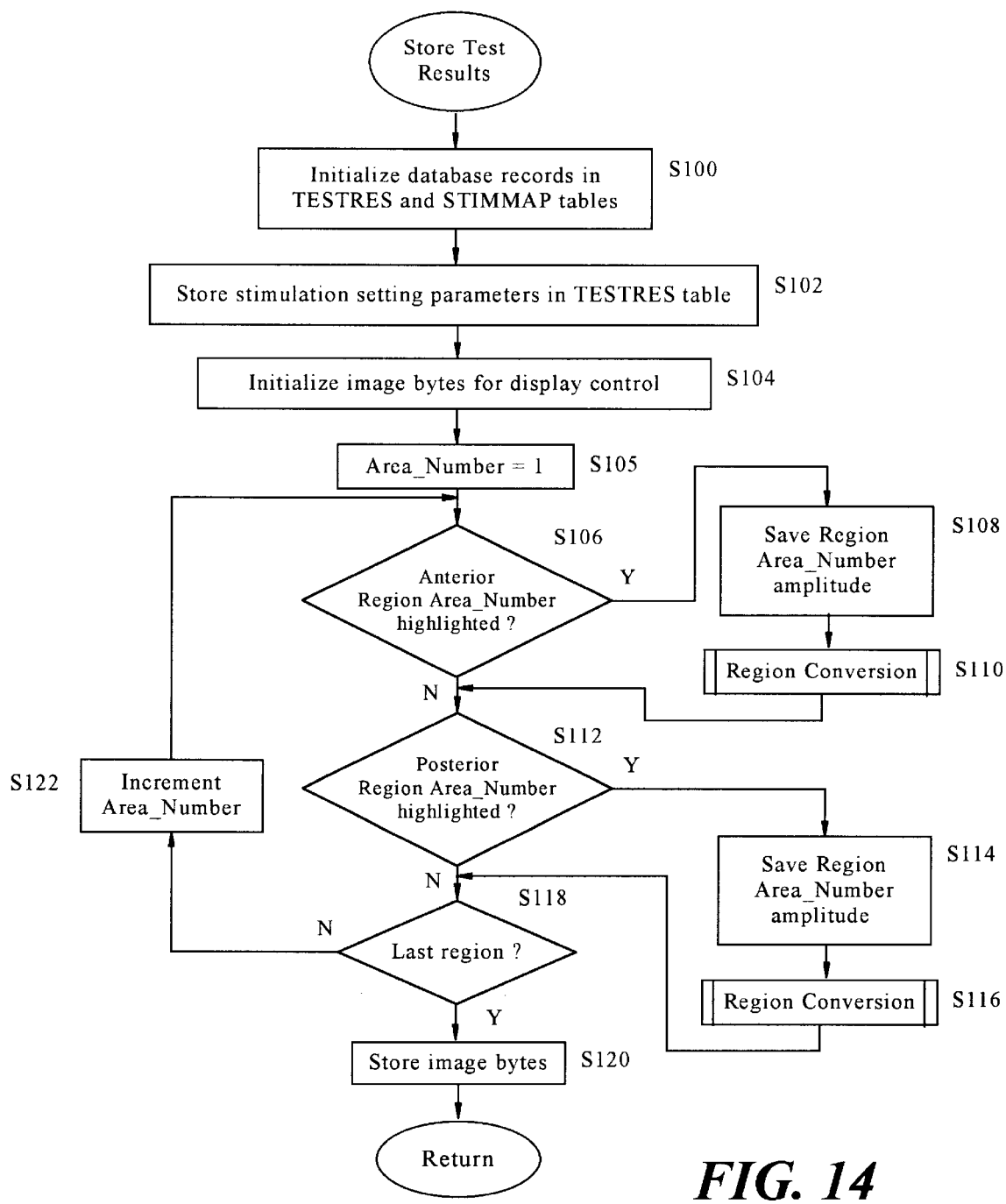
FIG. 14 is a flow chart algorithm for the storage of image-related data that comprises the anterior and posterior views of the bodily image graphic of FIG. 10.

Step #8: The defined stimulation parameters and related stimulation image is saved by actuating the "log setting" screen button (Region 212). The corresponding treatment parameter set is stored in portion 80 of TESTRES table 78 (Step S102 of FIG. 14, discussed hereinbelow), and data representative of the stimulation image are stored in portions 86 and 88 of STIMMAP table 82 (Steps S108 and S114 of FIG. 14, discussed hereinbelow). The stimulation image is preferably stored on a region-by-region basis and can be represented by binary data or an analog data. While not preferable, the image as a whole (i.e., a bitmap) could be stored. For each region of pain or variation in posture that may require a different stimulation setting, Steps 1–8 are repeated to obtain the necessary number of treatment parameter sets.

From the perception, bilateral, and motor amplitude values entered in the above steps, the software defines a minimum amplitude value and a maximum amplitude value for the corresponding stimulation setting. As shown in FIG. 4, these values are stored in each stimulation setting data file. While not within the scope of this disclosure, the software can further use the perception, bilateral, and motor amplitude values to calculate an initial stimulation amplitude, or a comfort amplitude. As but one example, the comfort amplitude is equivalent to the perception amplitude plus an incremental value, such incremental value being based on the bilateral and the motor amplitude values (e.g., 60% of a difference between the motor amplitude value and the bilateral value). The comfort amplitude can be downloaded and stored in association with a corresponding treatment parameter set.

Figure 11:
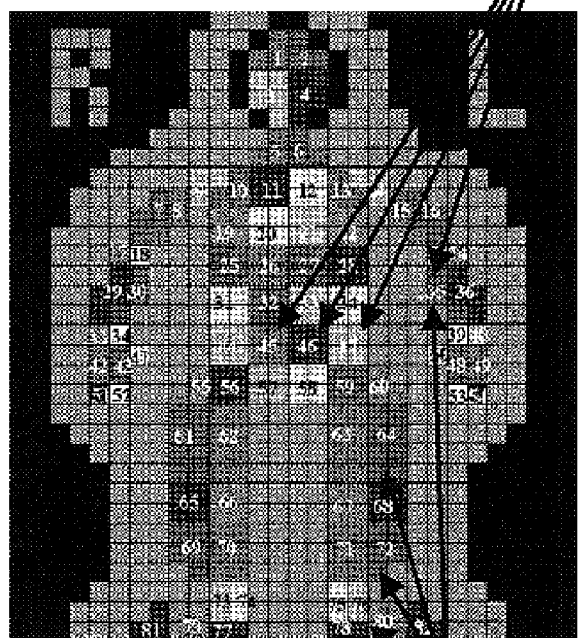
FIG. 11 illustrates a composite bodily graphic presentable on the display of the transmitter of FIG. 3, which is visually formed from data of the anterior and posterior views of the bodily image graphic of FIG. 10.

Further, as may be appreciated, the individual and composite stimulation graphics displayed on the display 50 of the transmitter 102 (see FIGS. 5, 6, and 7A–D) are derived from the stimulation images generated in the Steps #3, #5, and #7 described above (e.g., 40→40' and 42→42' in FIGS. 10 and 11). As the image of the computer-based images possess significantly greater resolution, however, these images must be reduced to correspond to the display 50 of the transmitter 102. However, as the stimulation image to be displayed on the transmitter 102 is intended to convey valuable information to a user concerning the effect of a stored, corresponding stimulation setting (i.e., an accurate representation of the stimulation images from the definition and testing session(s)), it is important that the conversion process not vitiate the significance of the data being converted.

For a description of the conversion process, reference will be made to FIGS. 9A and 10–15.

FIGS. 12 and 13 illustrate graphic conversion tables that provide a "road map" to effecting a graphical conversion from the graphical platform of the computer 128 to the graphical platform of the transmitter 102. The content of the conversion tables is a direct function of the display 50 and its display matrix.

As background for some of the numerical entries in the tables of FIGS. 12 and 13, the display 50 used in this example requires input command signals of a 1 byte form. Each byte represents a vertical column of eight pixels. Either a pixel is "on" or "off" based on the defining bits of each byte. Conventionally, "0" represents an off-state, and "1" represents an on-state. Further to the characteristics of the display 50, which is said to a 100 column by 32 row field for purposes of this description, addressing a particular column is made by particular reference to 1–100; however, addressing a particular row is achieved through "page" references. For example, "page 1" is the top page, or rows 1–8 of the display 50; "page 2" represents rows 9–16 of the display 50; "page 3" represents rows 17–24 of the display 50; and "page 4" is the bottom page, or rows 25–32 of the display 50. Moreover, the display related transfer protocol requires that for each "page," two image-forming instructions must be transferred—one instruction for the right side of the image, and one instruction for the left side of the image.

In view of these protocol-established boundaries of this exemplary embodiment, the following meanings can be imparted to the headings of the tables of FIGS. 11 and 12. FIG. 12 concerns ANTERIOR image regions, and FIG. 13 concerns POSTERIOR image regions.

Column 1: Region numbers that directly correspond to the regions of the stimulation images displayed on the computer 128 (FIG. 10).

Column 2: Anatomical description of each region.

Column 3: A value (0–3) that corresponds to the LCD positional "page" reference, described hereinabove.

Column 4: A value (1–20) that corresponds to a pixel column of the left portion of the image. When executed by the transmitter 102, an offset is applied to the value to allow the image to be properly positioned within the display 50.

Column 5: Decimal equivalent of the hexadecimal byte used to define a pixel representation for the left portion of the image being converted.

Column 6: A value (1–20) that corresponds to a pixel column of the right portion of the image. When executed by the transmitter 102, an offset is applied to the value to allow the image to be properly positioned within the display 50.

Column 7: Decimal equivalent of the hexadecimal byte used to define a pixel representation for the right portion of the image being converted.

Each conversion table sets forth an entry for each of the regions shown in the stimulation images (see FIGS. 10, 12, and 13). Notably, where left regions (and right regions) are converted and do not share pixel boundaries with another region, the Column 2 bit mask is set to zero. This allows the relevant left areas (and relevant right areas) to be masked appropriately without adding additional complexity to either the conversion tables or the controlling software. As may also be observed from the conversion tables, there is no provision for the conversion and transfer of the bodily representation displayed on the display 50. To avoid unnecessary data transfer, preferably such bodily representation is maintained in the transmitter 102, and thus is not contained in the converted data, or serial message.

In cooperation with the description of Step #8 for the process of real-time definition and testing described above, FIGS. 14 and 15 illustrate an algorithm to effect the conversion from the stimulation images of the computer 128 to the composite bodily image for the transmitter 102.

Upon actuating the "log setting" screen button (Region 212 of FIG. 9A; Step #8 of the process for real-time definition and testing), Step S100 initializes a database record in TESTRES and STIMMAP tables 78 and 82 (FIG. 8). In Step S102, the user-set treatment parameter set is stored in portion 80 of TESTRES table 78. In Step S104, twenty image bytes, for each of the four display pages of the display 50, are initialized as Page1Bytes, Page2Bytes, Page3Bytes, Page4Bytes. Prior to the actual storage activities, the Area_Number variable is reset in Step S105

The first of several decisions for this algorithm is made at Step S106. In particular, a specific region (i.e., Region Area_Number) of the anterior stimulation image., from Region 210 of the computer 128 (also FIG. 10), is analyzed to determine whether such region is highlighted. If the decision returns a "yes," the amplitude level for such region is stored in portion 86 of the STIMMAP table 82, and this region is subjected to a graphical conversion using the subroutine of FIG. 15 (described in detail below).

Upon concluding Step S110 (or receiving a "no" decision from Step S106), a determination is made whether the corresponding region of the posterior stimulation image, from the computer 128 (FIG. 10), is highlighted. If the decision returns a "yes," the amplitude level for such region is stored in portion 88 of the STIMMAP table 82, and this region is subjected to a graphical conversion also using the subroutine of FIG. 15.

After conclusion of Step S116 (or receiving a "no" decision from Step S112), an inquiry is made whether the last region of both the stimulation images has been considered (Step S118). If not ("no" in Step S118), the Area_ Number variable is increased by one (Step S122), and the routine returns to the decision of Step S106. Alternatively, if the last region has been considered ("yes" in Step S118), variables Page1Bytes, Page2Bytes, Page3Bytes, and Page4Bytes are stored in portion 84 of the STIMMAP table 82, and the routine is concluded.

Figure 15:
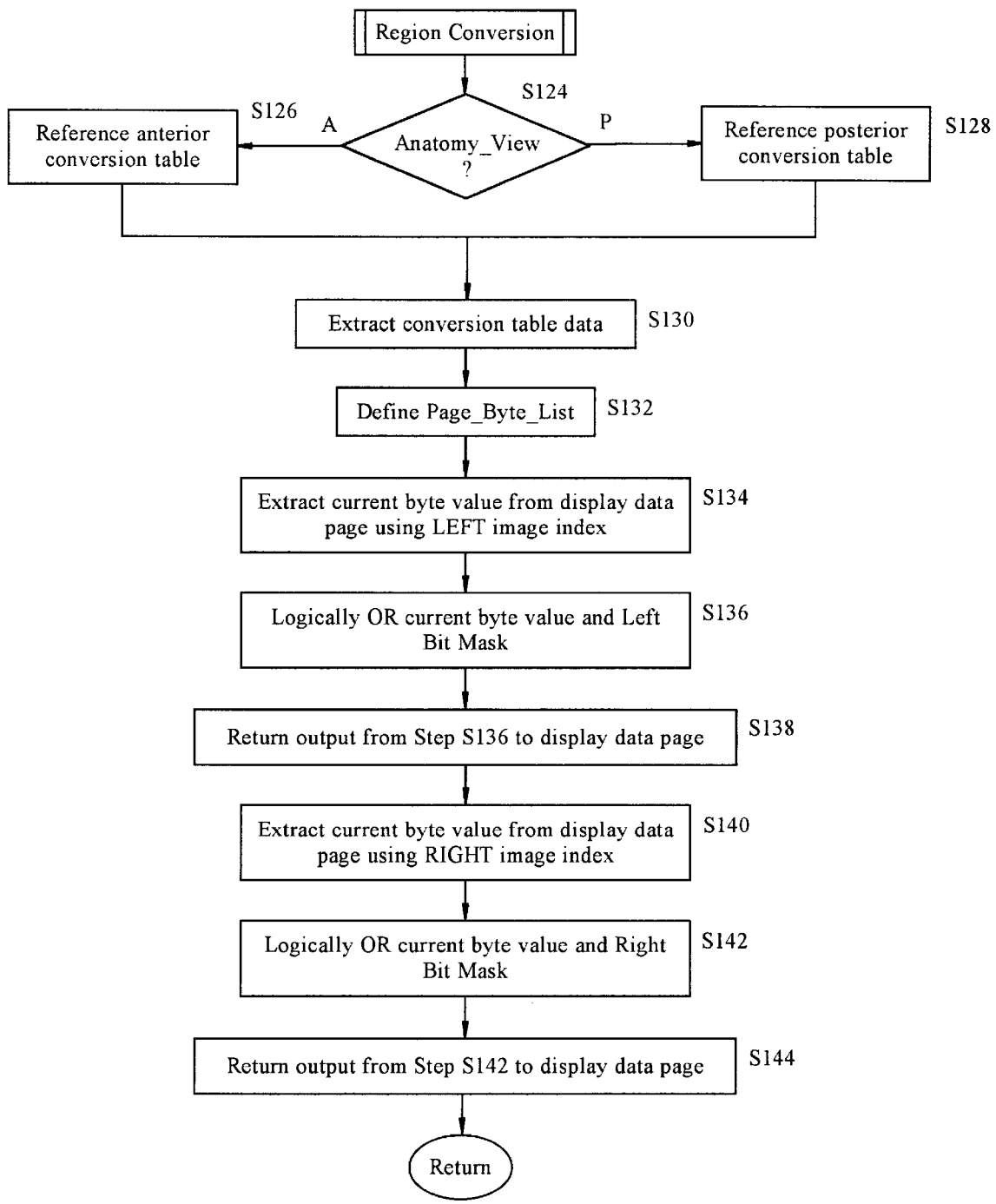
FIG. 15 is a flow chart algorithm for graphical image conversion from the anterior and posterior views of the bodily image graphic of FIG. 10 to the composite bodily graphic of FIG. 11.

In reference to the area conversion routine illustrated in FIG. 15, a decision is initially made at Step S124 whether the originating call to the subroutine came from Step S110 or Step S116, or more particularly, whether the subject region derives from the anterior stimulation image or the posterior stimulation image. If "anterior," the conversion table of FIG. 12 is referenced (Step S126), and alternatively, the conversion table of FIG. 13 is referenced (Step S128).

In Step S130, after correlating the Area Number variable and the values of Column 1 of the proper conversion table, values are extracted for the "Screen Display Page," "Left Side Column," "Left Bit Mask," "Right Side Column," and "Right Bit Mask." From the "Screen Display Page" value extracted in Step S130, the Page_Byte_List variable is equated to one of the Page1Bytes, Page2Bytes, Page3Bytes, and Page4Bytes variables in Step S132. In Step S134, the current byte value is extracted from the page defined by the Page_Byte_List variable. In this instance, the "Left Side Column" value is used as an index into the Page_Byte_List page. Step S136 effects a logical "ORing" of the extracted current byte value (from Step S134) and the "Left Bit Mask" value (from Step S130). The output of Step S136 is returned as the subject byte value to the Page_Byte_List page (Step S138).

In Step S140, the current byte value is extracted from the page defined by the Page_Byte_List variable using the "Right Side Column" value as an index into the Page_ Byte_List page. Step S142 effects a logical "ORing" of the extracted current byte value (from Step S140) and the "Right Bit Mask" value (from Step S130). The output of Step S142 is returned as the subject byte value to the Page Byte List page (Step S144). The routine returns following these conversion steps.

Consistent with the description of the algorithm of FIG. 15 and the illustration of FIG. 10, it should be noted that the regional segmentation of both the anterior image and the posterior image is designed to produce regionally-compatible images. Specifically, the anterior image and the posterior image should maintain the same number of regions, and the regions should be consistently arranged so that like-numbered (i.e., like-identified) regions will effectively merge upon the symmetrical overlay of the anterior and posterior images.

For at least this example, the composite bodily image displayable on the display 50 is provided with a number of regions numerically consistent with one of either the anterior or the posterior stimulation images from the computer 128. It is contemplated, however, that this will not always be achievable, wherein the composite bodily image for the transmitter 102 will be required to display an abridged version of the image data of the stimulation images. To this end, the algorithm of FIG. 15 would further be required to assess each region, and a number of adjacent region(s) (the number of adjacent regions being dependent upon the available resolution of the composite bodily graphic), for purposes of combining the graphical data of such regions for display in display 50.

While the above algorithm describes a graphical conversion process that occurs at the time of data storage, it should be appreciated that the timing for such conversion is not critical. Rather, the graphical conversion could instead occur at the time of downloading the stimulation settings and the program controls from the computer 128 to the transmitter 102.

Of further note, much of information conveyed here regarding the conversion algorithm is a function of the very specific display 50 chosen for the described embodiment. Consequently, it should be noted that substantive information within the conversion tables (FIGS. 12 and 13), described means for addressing the display 50 (e.g., 1 byte instructions, coordinate addressing based on columns and pages, etc.), and the like serve only as one exemplary form of the present invention. The use of other displays could alter these particular aspects of the above disclosure; however, any such substitution would not be outside the scope of the disclosed invention.

Therapy Definition

Upon completing the definition and testing of various stimulation parameters, all of the recorded stimulation settings are displayed in, and are available for selection through, Region 216 of the screen shot of FIG. 9B. Program, or therapy, creation is achieved by the following steps:

Step A: A program is selected from Region 226. Each program can be named using an alphanumeric designation (e.g., "sleeping," "sitting," "standing," etc.). Depending on the system, such alphanumeric designation may or may not be transferred to the transmitter 102. If transferred, such designation could be displayed in display 50. As but one example, such designation could be displayed in at least the program selection mode (FIGS. 7A–7D) to better assist a user in appreciating the intended purpose of each program in the event such purpose cannot be gleaned from the displayed composite graphic.

As an alternative to displaying the designation, the transmitter 102 could store the designation in memory for later transfer to a newly connected computer 128 to provide additional information to a reviewing physician.

Step B: With a program selected, a number of stimulation settings can then be selected from Region 216. As stated above, for a most preferred embodiment, no more than eight stimulation settings can be attributed to any one program.

Step C: With the desired stimulation setting(s) selected, the "Add Stim Set(s) to Prog." screen button (Region 218) is actuated. Upon actuation, the software effects the following actions: (i) corresponding stimulation setting(s) is/are added to the selected program; (ii) entries corresponding to the transferred stimulation settings are created in the STIMSET table 76, and links are established between such entries and the PROGRAMS table 74; and (iii) TESTRES and STIMMAP references are added to the new STIMSET records.

Step D: Upon completing the therapy definition, the "download programs" screen button (Region 222) can be actuated, and if so, the indicated programs, with related stimulation settings, are transferred to the connected transmitter 102.

During the download process, it is preferred that a status screen (FIG. 9C) be provided to inform the user as to the progress of the download. At least in the illustrated embodiment, at Region 224, stimulation graphics corresponding to at least the individual stimulation settings are shown as they are downloaded. Although the creation of a program's composite graphic (FIG. 5) can occur at any time after definition of the program, it is preferred that during the downloading process, the individual graphic regions of each stimulation settings are subject to a logical "ORing", and the result of such process is stored in the COMPOSITE GRAPHIC field of a program data file (FIG. 4).

General

While the above description focuses on the use of a general purpose computer (e.g., laptop or desktop systems), using conductive or alternative connection methods (e.g., infrared transmission, radio-frequency transmission, ultrasonic transmission, etc.), it should be appreciated that the "computer" of the present invention could equally be represented by a dedicated hand-held programmer or portable computing devices, e.g., Palm®-type devices, Windows™CE-based devices, and the like.

Although this disclosure has concentrated its examples on RF stimulation systems, there is no limitation that would prevent this invention from being applied to implanted pulse generator (IPG) systems that offer multiple stimulation settings or therapy programs.

While the above description further focuses on the present invention being used in the context of spinal cord stimulation systems, it should be noted that the present invention is equally applicable to any application that experiences the frustrations identified above for systems that store multiple applications without sufficient means to readily identify such applications. As but a few examples where the present invention might obviously benefit the current state of the art, deep brain stimulation (DBS), transcutaneous electrical nerve stimulation (TENS), pulsed electromagnetic stimulation (PEMS), biofeedback applications, and programmable drug delivery systems.

Although visual imagery is believed to impart the greatest understanding to a user in a limited-sized display, it is not beyond the scope of this invention that the displayed stimulation "graphic" consist of or include a textual description of the specific stimulation setting and/or program. Such textual description could be fully descriptive (e.g., "upper torso") or simply use abbreviations (e.g., "UT"). Moreover, the textual descriptions could be provided by the user at the time of defining and testing the stimulation parameters or at the time of assembling the various programs, or the computer could formulate such textual descriptions, from a listing of prescribed options, based on the data used to otherwise generate the transmitter-based graphics.

While the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A neuromodulation therapy system comprising:
   at least one multi-electrode, implantable stimulation lead adapted to effect delivery of electrical energy to proximately positioned tissue;
   an implantable receiver, connectable to the at least one stimulation lead, adapted to deliver electrical energy to the at least one stimulation lead in response to at least one instructional control signal; and
   a transmitter, separate from a general purpose computer and adapted to transmit said instructional control signal to the receiver, the transmitter comprising:
   a memory adapted to store at least two programs, each program comprising a plurality of treatment parameter sets, each treatment parameter set comprising a plurality of variables, said instructional control signal being generated in response to the plurality of variables, wherein each treatment parameter set includes identification information representative of a stimulation effect of that treatment parameter set;
   a setting modification control for enabling modification of one of the plurality of variables in one of the treatment parameter sets;
   a selector adapted to effect a selection of a stored program;
   a controller adapted to execute a selected one of said programs wherein the controller selectively converts the variables of each treatment parameter set of the selected one of said programs to respective control signals for transmission to the receiver; and
   a transmitter display, integral to the transmitter, wherein the identification information is displayed on the transmitter display.

2. A neuromodulation therapy system in accordance with claim 1, wherein the identification information is representative of a perceived stimulation effect corresponding to the treatment parameter set.

3. A neuromodulation therapy system in accordance with claim 1, wherein identification information is pictorial in form and is presented relative to an anatomical reference.

4. A neuromodulation therapy system in accordance with claim 1, wherein each program includes program-specific identification information and wherein the transmitter display displays the program specific information.

5. A neuromodulation therapy system in accordance with claim 4, wherein the program-specific identification information of a given program consists of a composition of the identification information of each of the treatment parameter sets within such program.

6. A neuromodulation therapy system in accordance with claim 1, wherein at least one of the treatment parameter sets defines an electrode polarity or off-state for each of the electrodes of the stimulation lead.

7. A neuromodulation therapy system in accordance with claim 1, wherein at least one of the treatment parameter sets specifies a signal waveform the defines, in part, the electrical energy delivered by the system.

8. A neuromodulation therapy system in accordance with claim 1, wherein the controller sequentially executes each treatment parameter set within the selected one of said programs.

9. A neuromodulation therapy system in accordance with claim 1, wherein the setting modification control enables selection of at least one of the treatment parameter sets.

10. A neuromodulation therapy system in accordance with claim 1, further comprising a general purpose computer connectable to the transmitter and adapted to generate anatomically-based images specifically depicting an effect of individual treatment parameter sets.

11. A neuromodulation therapy system comprising instruction transmission device, a receiver, and a delivery instrument, connectable to the receiver, adapted to effect delivery of a neuromodulation therapy to proximately positioned tissue, wherein the instruction transmission device is separate from a general purpose computer and is adapted to transmit control signals to the receiver to effect delivery of the neuromodulation therapy through the connected delivery instrument, the system further comprising:

a memory adapted to store at least two programs, each program comprising a plurality of instructions that individually characterize therapy-defining control signals, wherein each instruction includes identification information representative of a stimulation effect of the instruction;

a setting modification control for enabling modification of a defining attribute of one of the plurality of instructions;

a selector adapted to effect a selection of one of the stored programs;

a controller adapted to execute the selected one of the stored programs, wherein the controller converts an instruction of the selected one of the stored programs to corresponding control signals for transmission to the receiver; and a transmitter display, integral to the transmitter, wherein the identification information is displayed on the transmitter display.

12. A tissue stimulation system comprising a transmitter, a receiver adapted to be implanted within a patient, and a least one multi-electrode, implantable stimulation lead, electrically connectable to the receiver, wherein the transmitter is separate from a general purpose computer and is adapted to transmit stimulation data to the receiver, which effects delivery of electrical energy through the connected stimulation lead, such electrical energy being provided in response to stimulation data, the system further comprising:

a memory adapted to store at least two programs, each program comprising a plurality of said stimulation settings, wherein each stimulation setting includes specific information representative of a stimulation effect corresponding to the stimulation setting;

a setting modification control for enabling modification of a defining attribute of one of the stimulation settings;

a selector adapted to effect a selection of one of the at least two programs;

a controller adapted to execute a selected one of the at least two programs, wherein the controller converts the plurality of stimulation settings of the selected program into the stimulation data for transmission to the receiver; and a transmitter display, integral to the transmitter, wherein the setting specific information is displayed on the transmitter display.

13. A tissue stimulation system in accordance with claim 12, wherein the specific information is representative of a patient-perceived stimulation effect corresponding to a related stimulation setting.

14. A tissue stimulation system in accordance with claim 12, wherein the specific information corresponds to a visual anatomical reference.

15. A tissue stimulation system in accordance with claim 12, wherein each program further comprises program-specific information and wherein the transmitter display displays the setting-specific information.

16. A tissue stimulation system in accordance with claim 15, wherein the program-specific information of a given program consists of a composition of the setting-specific information of each of the stimulation settings with such program.

17. A tissue stimulation system in accordance with claim 12, wherein one of the plurality of stimulation settings is converted to stimulation data to provide an electrode polarity or off-state for each of the electrodes of the stimulation lead.

18. A tissue stimulation system in accordance with claim 12, wherein one of the plurality of stimulation settings is converted to stimulation data to provide a signal waveform that defines, in part, the electrical energy delivered by the system.

19. A tissue stimulation system in accordance with claim 12, wherein the controller sequentially executes each stimulation setting within a selected program.

20. A tissue stimulation system in accordance with claim 12, wherein the setting modification control enables selection of one of the plurality of stimulation settings.

21. A tissue stimulation system in accordance with claim 20, wherein one of the plurality of stimulation settings is an amplitude value.

22. A tissue stimulation system in accordance with claim 12, further comprising a general purpose computer, connectable to at least the transmitter, adapted to define and to supply stimulation settings to the transmitter.

23. A tissue stimulation system in accordance with claim 12, further comprising a general purpose computer, connectable to at least the transmitter, adapted to define the programs and to supply the programs to the transmitter.

24. A tissue stimulation system in accordance with claim 12, further comprising a general purpose computer, connectable to at least the transmitter, adapted to generate anatomically-based images specifically depicting an effect of individual stimulation settings.

* * * * *

UNITED STATES PATENT AND TRADEMARK OFFICE
CERTIFICATE OF CORRECTION

PATENT NO. : 6,748,276 B1
DATED : June 8, 2004
INVENTOR(S) : Daignault et al.

It is certified that error appears in the above-identified patent and that said Letters Patent is hereby corrected as shown below:

Title page,
Item [75], Inventor, please add -- George Van Campen Ft. Lauderdale, FL (US) --

Signed and Sealed this

Twenty-second Day of March, 2005

JON W. DUDAS
*Director of the United States Patent and Trademark Office*